United States Patent
Shoulders et al.

(10) Patent No.: US 10,946,361 B2
(45) Date of Patent: Mar. 16, 2021

(54) COMPOSITIONS AND METHODS FOR SELECTIVELY SEQUESTERING METAL IONS

(71) Applicant: Massachusetts Institute of Technology, Cambridge, MA (US)

(72) Inventors: Matthew D. Shoulders, Cambridge, MA (US); Stephen J. Lippard, Washington, DC (US); Elizabeth Marie Nolan, Cambridge, MA (US); Christopher E. R. Richardson, Boston, MA (US); Lisa S. Cunden, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 225 days.

(21) Appl. No.: 15/866,179

(22) Filed: Jan. 9, 2018

(65) Prior Publication Data
US 2019/0210005 A1 Jul. 11, 2019

(51) Int. Cl.
*B01J 20/32* (2006.01)
*C08L 5/12* (2006.01)
*C07K 14/47* (2006.01)

(52) U.S. Cl.
CPC .......... *B01J 20/3274* (2013.01); *C07K 14/47* (2013.01); *C08L 5/12* (2013.01); *B01D 2257/60* (2013.01)

(58) Field of Classification Search
CPC ............. B01J 20/32; C07K 14/47; C08L 5/12
See application file for complete search history.

(56) References Cited

U.S. PATENT DOCUMENTS 9,255,019 B2    2/2016 He et al.
2004/0185042 A1* 9/2004 Scheiflinger ......... C07K 14/755
                                                                424/140.1

OTHER PUBLICATIONS

Goyette et al. "Pleiotropic roles of S100A12 in coronary atherosclerotic plaque formation and rupture" (J Immunol, 2009, 183, pp. 593-603). (Year: 2009).*
Specification Sheet 20266 (CarboxyLink Coupling Gel, Thermo Scientific, 2017) (Year: 2017).*
Specification Sheet 26196 (NHS-Activated Agarose Dry Resin, Thermo Scientific, 2014) (Year: 2014).*
Besold et al., Role of Calprotectin in Withholding Zinc and Copper from Candida albicans. Infect. Immun. Feb. 2018;86:e00779-17. 16 pages. Epub Nov. 13, 2017.
Cunden et al., Biochemical and Functional Evaluation of the Intramolecular Disulfide Bonds in the Zinc-Chelating Antimicrobial Protein Human S100A7 (Psoriasin). Biochemistry. 2017;56(43):5726-38. Epub Oct. 4, 2017.
Cunden et al., Bioinorganic Explorations of Zn(II) Sequestration by Human S100 Host-Defense Proteins. Biochemistry. 2018;57(11):1673-80. Epub Jan. 30, 2018.
Cunden et al., Calcium ions tune the zinc-sequestering properties and antimicrobial activity of human S100A12. Chemical Science. 2016;7:1338-48. Epub Oct. 26, 2016.
Hadley et al., Biochemical and Spectroscopic Observation of Mn(II) Sequestration from Bacterial Mn(II) Transport Machinery by Calprotectin. J. Am. Chem. Soc. 2018;140(1):110-3. Epub Dec. 6, 2017.

(Continued)

*Primary Examiner* — Ryan B Huang
(74) *Attorney, Agent, or Firm* — Wolf, Greenfield & Sacks, P.C.

(57) ABSTRACT

Compositions and methods for the selective sequestration of metal ions are generally described.

9 Claims, 11 Drawing Sheets

Specification includes a Sequence Listing.

(56) References Cited

OTHER PUBLICATIONS

Knight et al., Development of peptoid-based ligands for the removal of cadmium from biological media. Chem. Sci. 2015;6:4042-8. Epub May 14, 2015.

Lowe et al., Report of the International Society for Zinc Biology 5th Meeting, in Collaboration with Zinc-Net (COST Action TD1304)—UCLan Campus, Pyla, Cyprus. Int. J. Mol. Sci. Dec. 2017;18(12):2518. 5 pages.

Nakashige et al,. Nickel Sequestration by the Host-Defense Protein Human Calprotectin. J. Am. Chem. Soc. 2017;137:8828-36. Epub Jun. 2, 2017.

Nakashige et al., Human calprotectin is an iron-sequestering host-defense protein. Nature Chemical Biology. Oct. 2015;11:765-71. Epub Aug. 24, 2015.

Nakashige et al., The Hexahistidine Motif of Host-Defense Protein Human Calprotectin Contributes to Zinc Withholding and Its Functional Versatility. J. Am. Chem. Soc. 2016;138:12243-51. Epub Aug. 19, 2016.

Richardson et al., A Method for Selective Depletion of Zn(II) Ions from Complex Biological Media and Evaluation of Cellular Consequences of Zn(II) Deficiency. J. Am. Chem. Soc. 2018;140(7):2413-6. Epub Jan. 16, 2018. Supporting Information Included.

Zhou et al., A protein engineered to bind uranyl selectively and with femtomolar affinity. Nature Chemistry. 2014;6:236-41. Epub Jan. 26, 2014.

\* cited by examiner

COMPOSITIONS AND METHODS FOR SELECTIVELY SEQUESTERING METAL IONS

GOVERNMENT SPONSORSHIP

This invention was made with Government support under Grant Nos. R01AR071443 and R01-GM065519 awarded by the National Institutes of Health, and Grant No. CHE-1352132 awarded by the National Science Foundation. The Government has certain rights in the invention.

TECHNICAL FIELD

Compositions and methods for selectively sequestering metal ions using protein molecules immobilized on a support are generally described.

BACKGROUND

Selective sequestration of metal ions from diverse biological media is essential to study the mechanistic basis of many metal-dependent biological processes. For instance, selective depletion of a particular metal ion from mammalian cell culture medium (a solution that contains nutrients sufficient for mammalian cell proliferation) enables the study of the effects of deficiencies of that metal in metazoan cells. Reliable methods to deplete specific metals could also prove valuable in biomedical applications. A major obstacle in studying the roles of metals in biological systems is that reliable, user-friendly, and economical methods to deplete biological media of a particular metal are not available. Available strategies that are used to study the effects of metal deficiencies are described below along with caveats associated with the use of each method.

One existing strategy is to nonspecifically sequester metals in biological media using resin-supported chelators, and then to add back all metal ions except the target metal(s) to be depleted. Precise execution of this repletion mandates quantitation of medium metal content before and after chelator treatment, but even careful metal repletion may not recover the metal ion speciation of untreated mediums.

Another approach used to study metal deficiency is to treat cells with a cell-permeable, unsupported chelator, such as N,N,N',N'-tetrakis(2-pyridylmethyl)ethylenediamine (TPEN). Troublingly, TPEN has a high affinity for many d-block metal ions, and can inhibit the activity of metalloproteins. The risk of TPEN inhibiting metalloenzymes or affecting other metal-dependent processes precludes the use of TPEN as a reliable proxy for metal sequestration.

A third strategy to study the effect of deficiency of a particular metal ion on cellular phenotypes is to obtain a custom, well-defined cell culture medium that already lacks the target metal(s) to be depleted. This approach can be expensive, and only a subset of cells can be cultured in such media.

The above approaches and related alternatives each have caveats that hamper study of the consequences of metal deficiencies. Moreover, none of the above methods is user-friendly, cost-effective, or reliable. Accordingly, improved methods and compositions for metal sequestration are needed.

SUMMARY

Compositions and methods relating to the sequestration of metal ions using protein molecules immobilized on a support are generally described. According to certain embodiments, a plurality of protein molecules immobilized on a support can be used to selectively sequester metal ions from a sample comprising the metal ions. In some embodiments, the plurality of protein molecules immobilized on a support is exposed to a sample comprising a plurality of a first type of metal ion and a plurality of a second type of metal ion, wherein greater than about 90% of the plurality of a first type of metal ion in the sample are sequestered and less than about 5% of the plurality of a second type of metal ion in the sample are sequestered. The subject matter of the present invention involves, in some cases, interrelated products, alternative solutions to a particular problem, and/or a plurality of different uses of one or more systems and/or articles.

Certain embodiments relating to a composition are described, wherein the composition comprises a plurality of S100 protein molecules and a support, wherein the plurality of S100 protein molecules are immobilized on the support.

According to some embodiments, a method is described, comprising exposing a composition to a sample comprising a plurality of a first type of metal ion and a plurality of a second type of metal ion, wherein the composition comprises a plurality of protein molecules immobilized on a support, and wherein following the exposing step, greater than about 90% of the first type of metal ion in the sample are sequestered by the plurality of protein molecules immobilized on a support, and less than about 5% of the second type of metal ion in the sample are sequestered by the plurality of protein immobilized on a support.

In some embodiments, a method is described, comprising exposing a composition to a regeneration agent, wherein the composition comprises a plurality of protein molecules immobilized on a support and a plurality of a first type of metal ions associated with the plurality of protein molecules, and wherein following the exposing step, less than 5% of the plurality of a first type of metal ions remain associated with the plurality of protein molecules.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
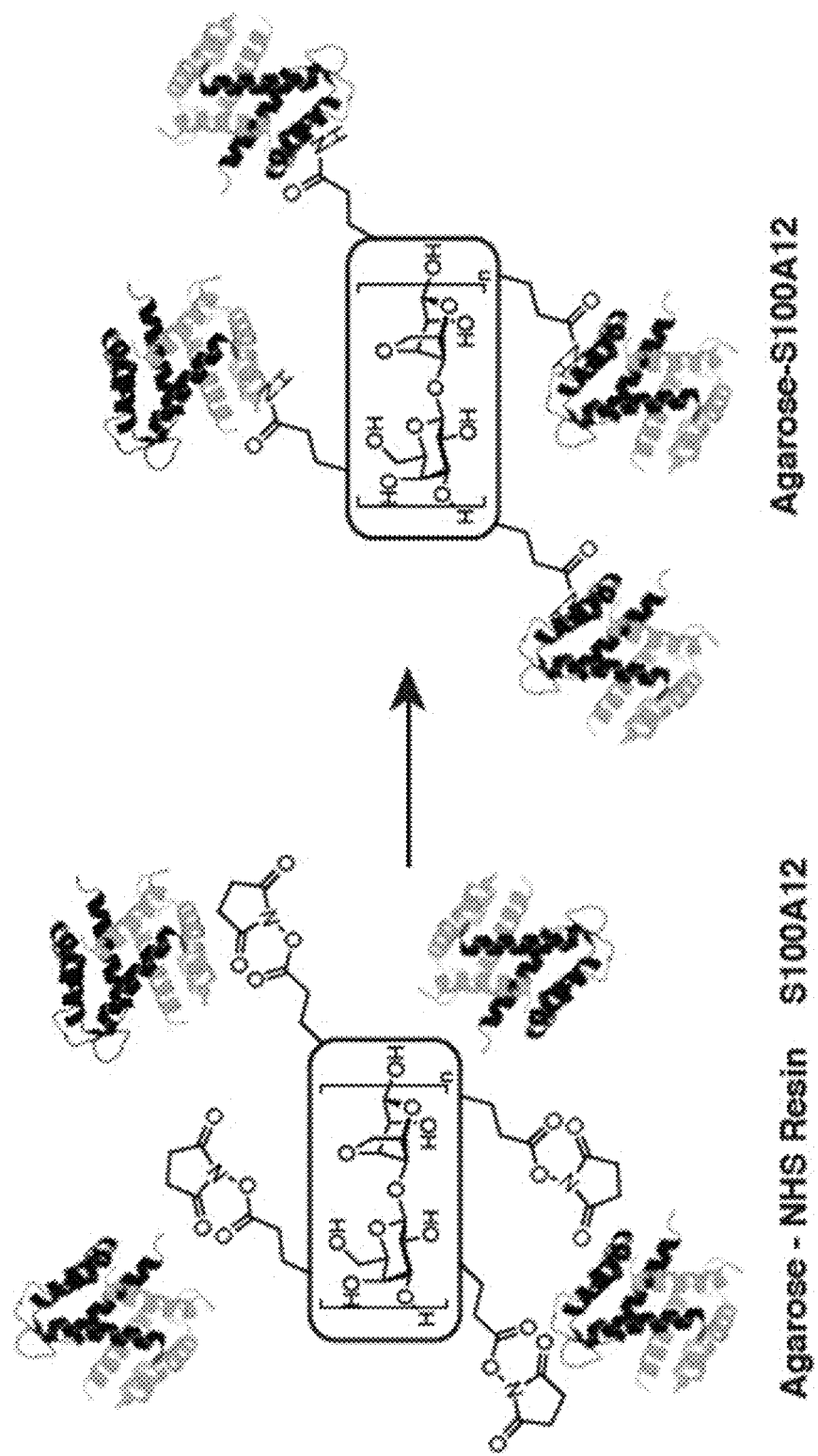
FIG. 1 shows, according to certain embodiments, an exemplary drawing of a protein immobilized on a support.

Compositions and methods for the selective sequestration of metal ions are generally described.

According to certain embodiments, a plurality of protein molecules immobilized on a support, such as an agarose resin, are exposed to a sample comprising a plurality of a first type of metal ion and a plurality of a second type of metal ion. The composition comprising the plurality of protein molecules immobilized on a support can, in certain embodiments, selectively sequester metal ions from the sample. For example, greater than about 90% of the plurality of a first type of metal ion in the sample is sequestered by the plurality of protein molecules immobilized on a support and less than about 5% of the plurality of a second type of metal ion in the sample is sequestered by the plurality of protein molecules immobilized on a support. According to some embodiments, the sample comprising a plurality of a first type of metal ion and a plurality of a second type of metal ion is a biological medium. The plurality of protein molecules immobilized on a support can selectively sequester (e.g., chelate) one type of metal ion from the sample comprising a plurality of a first type of metal ion and at least a plurality of a second type of metal ion. As used herein, the term "plurality" refers to two or more (i.e., at least two).

It should be understood, that while many of the embodiments described herein refer to sample comprising a plurality of a first type of metal ion and at least a plurality of a second type of metal ion, this instance is by no means limiting, and the sample may comprise more than two types of metals ions. For example, the sample may comprise a plurality of at least three types of metal ions, or a plurality of at least four types of metal ions, or a plurality of at least five types of metal ions, or a plurality of at least ten types of metal ions, or a plurality of at least fifteen types of metal ions, or more. In such embodiments, greater than about 90% (or other values described herein) of the plurality of a first type of metal ion in the sample may be sequestered by the plurality of protein molecules immobilized on a support and less than about 5% (or other values described herein) of each of the other types of metal ion in the sample may be sequestered by the plurality of protein molecules immobilized on a support.

In one set of embodiments, following immobilization of the plurality of the first type of metal ion to the plurality of protein molecules immobilized on a support, the plurality of protein molecules immobilized on a support may be regenerated. That is, the plurality of the first type of metal ions may be removed or substantially removed from the protein molecules immobilized on a support, such that the protein molecules immobilized on a support may be reused. In some embodiments, the plurality of protein molecules may be regenerated via exposure to a regeneration agent to remove the plurality of a first type of metal ion that were sequestered. In certain embodiments, the regeneration agent is an acid that dissociates bound metal from the plurality of protein molecules immobilized on a support. According to some embodiments, the plurality of protein molecules immobilized on a support is then regenerated, and can be subjected to multiple sequestration cycles to sequester a plurality of metal ions from the same sample, or a new sample. In some embodiments, these methods and compositions may be used to determine the amount of metal ions in a sample, as described in more detail herein.

Certain embodiments are related to a composition comprising a plurality of protein molecules and a support, wherein the plurality of protein molecules is immobilized with respect to the support. In some embodiments, examples of proteins include S100 proteins and examples of supports include resins. Other embodiments of proteins and supports will be described herein in greater detail. According to certain embodiments, the composition comprises more than one protein molecule (e.g., 2, 5, 10, 20, 50, 100, 200, 300, 400, 500, or more protein molecules) immobilized with respect to a support. As used herein, the term "immobilized" is given its ordinary meaning in the art and refers to the attachment of a first species (e.g., a plurality of protein molecules) to a second, solid-phase, species (e.g., a support). The plurality of protein molecules can be immobilized on a support by any of a variety of suitable methods, which will be described in greater detail herein, including, but not limited to, methods such as covalently binding the plurality of protein molecules to a support and/or cross-linking the plurality of protein molecules to a support. FIG. 1 shows, according to certain embodiments, an exemplary drawing of a protein immobilized on a support. In FIG. 1, each exemplary protein, S100A12, is immobilized on a support (agarose resin) via formation of a covalent bond.

According to certain embodiments, the plurality of protein molecules are any of a variety of suitable proteins for the sequestration of metals. In some embodiments, the plurality of protein molecules is a plurality of protein molecules that can bind (e.g., chelate) metals. For example, the plurality of protein molecules comprises a plurality of S100A12 protein molecules. Further non-limiting embodiments include a plurality of S100A7, S100A8, or S100A9 protein molecules.

Certain embodiments are related to a plurality of S100A12 protein molecules. As used herein, the term "S100A12" (also referred to as "S100-A12," "calgranulin C," "MRP-6," "MRP6," "P6," "CAGC," "CGRP," "CO—Ag," "CAAF-1," and "EN-RAGE") refers to a member of the S100 family of proteins containing two EF-hand calcium-binding motifs. For example, see Cunden, L. S.; Gaillard, A.; Nolan, E. M., Chem. Sci., 2016, 7, 1338, Calcium ions tune the zinc-sequestering properties and antimicrobial activity of human S100A12", which is incorporated herein by reference in its entirety. Any S100A12 ortholog may be used with the methods and compositions described herein including, but not limited to, an S100A12 protein from any mammal such as a human, non-human primate, livestock animal (e.g., a pig, cow, sheep, or horse), or domesticated animal (e.g., a cat or dog). In certain embodiments, the S100A12 protein corresponds to NCBI reference sequence NP_005612.1 (SEQ ID NO: 1; protein) or NM_005621.1 (SEQ ID NO: 2; mRNA).

```
>NP_005612.1 protein S100-A12 [Homo sapiens]
                                          (SEQ ID NO: 1)
MTKLEEHLEGIVNIFHQYSVRKGHFDTLSKGELKQLLTKELANTIKNIKD
KAVIDEIFQGLDANQDEQVDFQEFISLVAIALKAAHYHTHKE >NM_005621.1 Homo sapiens S100 calcium binding
protein A12 (S100A12), mRNA
                                          (SEQ ID NO: 2)
ACCACTGCTGGCTTTTTGCTGTAGCTCCACATTCCTGTGCATTGAGGGGT

TAACATTAGGCTGGGAAGATGACAAAACTTGAAGAGCATCTGGAGGGAAT

TGTCAATATCTTCCACCAATACTCAGTTCGGAAGGGGCATTTTGACACCC

TCTCTAAGGGTGAGCTGAAGCAGCTGCTTACAAAGGAGCTTGCAAACACC

ATCAAGAATATCAAAGATAAAGCTGTCATTGATGAAATATTCCAAGGCCT

GGATGCTAATCAAGATGAACAGGTCGACTTTCAAGAATTCATATCCCTGG

TAGCCATTGCGCTGAAGGCTGCCCATTACCACACCCACAAAGAGTAGGTA

GCTCTCTGAAGGCTTTTTACCCAGCAATGTCCTCAATGAGGGTCTTTTCT

TTCCCTCACCAAAACCCAGCCTTGCCCGTGGGAGTAAGAGTTAATAAAC

ACACTCACGAAAAGTT

>Sequence of Human S100A12 for expression in BL21
(DE3) E. coli
                                          (SEQ ID NO: 3)
ATGACGAAACTGGAAGAACACTTGGAAGGCATTGTTAACATTTTTCATCA

ATACAGCGTGCGTAAGGGCCACTTCGACACCCTGAGCAAAGGTGAGTTGA

AACAGCTGCTGACCAAAGAGCTGGCAAATACGATCAAGAATATCAAGGAT

AAGGCTGTCATTGACGAGATTTTCCAGGGTCTGGATGCCAACCAAGACGA

GCAAGTTGATTTCCAGGAGTTTATCTCCCTGGTGGCGATCGCGCTGAAGG

CAGCGCACTATCATACCCACAAAGAATAA
```

Those of ordinary skill in the art will be aware of other suitable proteins that may be employed, for example, other S100-family proteins. Non-limiting examples of other suitable proteins may be disclosed in the following, herein incorporated by reference: e.g., see Besold, A. M.; Gilson, B. A.; Radin, J. N.; Ramsoomair, C.; Culbertson, E. M.; Li, C. X.; Cormack, B. P.; Cazin, W. J.; Kehl-Fie, T. E.; Culotta, V. C., Infect. Immun. 2017, ASAP, "The role of calprotectin in withholding zinc and copper from *Candida albicans*"; Cunden, L. S.; Brophy, M. B.; Rodriguez, G. E.; Flaxman, H. A.; Nolan, E. M., Biochemistry 2017, 56, 5726, "Biochemical and Functional Evaluation of the Intramolecular Disulfide Binds in the Zinc-Chelating Antimicrobial Protein Human S100A7"; Nakashige, T. G.; Zygiel, E. M.; Drennan, C. L.; Nolan, E. M., J. Am. Chem. Soc. 2017, 139, 8828, "Nickel Sequestration by the Host-Defense Protein Human Calprotectin"; Nakashige, T. G.; Stephan, J. R.; Cunden, L. S.; Brophy, M. B., J. Am. Chem. Soc. 2017, ASAP, "The Hexahistidine Motif of Host-Defense Protein Human Calprotectin Contributes to Zinc Withholding and Its Functional Versatility"; Cunden, L. S.; Gaillard, A.; Nolan, E. M., Chem. Sci. 2016, 7, 1338, "Calcium ions tune the zinc-sequestering properties and antimicrobial activity of human S100A12"; Nakashige, T. G.; Zhang, B.; Krebs, C.; Nolan, E. M., Nat. Chem. Bio. 2015, 11, 765, "Human calprotectin is an iron-sequestering host-defense protein"; Zhou, L.; Bosscher, M.; Zhang, C.; Özçubukçu, S.; Zhang, L.; Zhang, W.; Li, C. J.; Liu, J.; Jensen, M. P.; Lai, L.; He, C., Nature Chemistry, 2014, 6, 236, "A protein engineered to bind uranyl selectively and with femtomolar affinity", and U.S. Pat. No. 9,255,019 B2 to He et al.

The plurality of protein molecules can be immobilized on a support by any of a variety of suitable methods. For example, according to certain embodiments, the plurality of protein molecules can be immobilized on a support by binding the plurality of protein molecules to the support, entrapment of the plurality of protein molecules in/on the support, and/or cross-linking the plurality of protein molecules and attaching the cross-linked plurality of protein molecules to the support.

According to certain embodiments, immobilization of the plurality of protein molecules to a support (e.g., insoluble silica gel) can be done covalently. In some embodiments, the plurality of protein molecules covalently bound to a support is the strongest protein-to-support interaction. In some cases, other methods of immobilization include entrapment, in which an enzyme is trapped in a support (e.g., calcium alginate beads). According to some embodiments, other methods of immobilization include aggregating a plurality of protein molecules by cross-linking, in which a plurality of protein molecules are covalently bound to each other in order to generate a matrix consisting or a plurality of protein molecules, which are then attached (e.g., by covalent bonding) to a support.

In some embodiments, the plurality of protein molecules are immobilized with respect to the support via formation of at least one bond between each protein molecule and the support. Non-limiting examples of types of bond include an ionic bond, a covalent bond (e.g. carbon-carbon, carbon-oxygen, oxygen-silicon, sulfur-sulfur, phosphorus-nitrogen, carbon-nitrogen, metal-oxygen or other covalent bonds), a hydrogen bond (e.g., between hydroxyl, amine, carboxyl, thiol and/or similar functional groups, for example), a dative bond (e.g. complexation or chelation between metal ions and monodentate or multidentate ligands), Van der Waals interactions, and the like. In some embodiments, each protein molecules is immobilized with respect to the support via formation of at least one covalent bond.

Those of ordinary skill in the art will be aware of methods and techniques for covalently associating a plurality of protein molecules with respect to a support. For example, each of the plurality of protein molecules may be modified to include a residue (e.g., cysteine) that allows for covalent attachment to a support (e.g., silica gel).

As another example, methods of immobilizing the proteins to a support include protein modification using protein tags, which are known to those of ordinary skill in the art and generally refer to specific amino acid sequences that can be integrated into proteins to enhance the affinity of the protein for a particular species (i.e. enable metal affinity chromatography). For example, according to some embodiments, a plurality of protein molecules may be immobilized on a support using protein tags that allow for selective covalent or noncovalent attachment of proteins to another species (e.g., the support). Non-limiting examples of protein tags include $His_6$-tag/nickel-NTA, glutathione-S-transerase/glutathione, and maltose binding protein/maltose. According to certain embodiments, the plurality of proteins may be immobilized on a support by biotin-avidin and/or biotin-steptavidin interactions.

In some embodiments, the plurality of proteins may be immobilized on a support by any of a variety of bioconjugation techniques between the plurality of proteins and the support. For example, according to certain embodiments, cysteine residues of the plurality of proteins may react with iodoacetamides. In some embodiments, cysteine residues of the plurality of proteins may reversibly undergo addition to $\alpha$-$\beta$-unsaturated carbonyls. In some cases, cysteine residues of the plurality of proteins may reversibly add to maleimdies. According to certain embodiments, lysine residues of the plurality of proteins may react with isothiocyanates. Other methods and techniques will be known to those of ordinary skill in the art.

The term support, as used herein, generally refers to a material to which the plurality of protein molecules can be immobilized. According to certain embodiments, by immobilizing soluble proteins on supports, the protein can be used for longer periods of time and may have applications in industrial reactors. In certain embodiments, protein molecules immobilized on a support have improved reactivity, stability, and selectively towards substrates and/or compounds of interests compared to the unbound protein. According to some embodiments, a support may be a solid support. Examples of a solid support include carbon, alumina, silica, polymers, glass surfaces, inorganic support materials, resins, and the like. Combinations of the above referenced materials are also possible.

The solid support may have any suitable size or shape. For example, according the certain embodiments, the solid support may be square, rectangular, triangular, or, circular. In some embodiments, the solid support may comprise a plurality of particles (e.g., beads, nanostructures, and the like). In some embodiments, the solid support may be porous. According to certain embodiments, the solid support may be non-porous.

In some embodiments, the solid support is a resin. Non-limiting examples of a resin include polystyrene resin, polyamide resin, poly(ethylene glycol) resin, agarose resin, and the like. In some embodiments, the resin is agarose resin.

According to certain embodiments, a support may be modified to allow for the plurality of protein molecules to be immobilized with respect to the support (e.g., via formation of a covalent bond). In some embodiments, a support may be modified in any of a variety of suitable ways. For example, in some embodiments, the support may be modified with a plurality of functional groups that allow for association of the protein molecules with the support. In certain embodiments, the support may be modified with a plurality of functional groups that specifically allow for covalent attachment of the protein molecules. For example, according to some embodiments, agarose resin may be modified with N-hydroxy-succinimide (NHS) functional groups. In certain embodiments, protein molecules may react with (e.g., bind to) a NHS group, thereby forming a covalent bond and immobilizing the protein molecule with respect to the support. According to certain embodiments, the ester bond of an NHS group will specifically covalently bond with a primary amine of a protein (e.g. primary amine of S100A12), forging a stable amide linkage between the protein and support.

According to some embodiments, supports may be modified in other ways not relating to the binding of a plurality of protein molecules. In certain embodiments, a support (e.g., a resin) may be cross-linked. According to certain embodiments, a cross-linked support benefits from properties such as improved mechanical stability, diffusion, and swelling properties. Furthermore, in some cases, a cross-linked support induces some sites of permanent entanglement, which maintains the structural integrity of the support. In certain other embodiments, a support may be modified with a linker, which would connect a support to a second material (e.g., another support). An example of a linker may be an activated surface functional group.

Some embodiments of the invention are related to a method of selectively sequestering metal ions, wherein the plurality of protein molecules immobilized on a support (herein referred to as "the protein/support composition") described herein is exposed to a sample comprising a plurality of a first type of metal ion and a plurality of a second type of metal ion. As used herein, the term "sequester" is given its ordinary meaning in the art and can be referred to as the formation of a stable composition by binding of a first moiety (e.g., a metal) to a second moiety (e.g., a protein). In some embodiments, the first moiety (e.g., the metal) is no longer available for reactivity.

Exposing the protein/support composition to a sample comprising a plurality of a first type of metal ion and a plurality of a second type of metal ion may be carried out using any of a variety of suitable methods known to those skilled in the art. For example, the exposing step may comprise incubation of the protein/support composition and the sample comprising a plurality of a first type of metal ion and a plurality of a second type of metal ion.

In certain other embodiments, the exposing step comprises other methods, such as passing the sample comprising a plurality of a first type of metal ion and a plurality of a second type of metal ion over the protein/support composition. For example, according to some embodiments, the protein/support composition is in direct contact with the sample solution comprising the plurality of a first type of metal ion and a plurality of a second type of metal ion. In certain embodiments, the sample can flow through, over, under, and/or by the protein/support composition. In certain embodiments, the protein/support composition is set up in a chromatography column, and a solution comprising the plurality of a first type of metal ion and a plurality of a second type of metal ion is passed through the chromatography column and therefore in contact with the protein/support composition.

For example, in some embodiments, exposing the protein/support composition to a sample comprising a plurality of a first type of metal ion and a plurality of a second type of metal ion comprises any of a variety of suitable times. According to certain embodiments, the exposing step is done for greater than about 5 minutes, greater than about 10 minutes, greater than about 15 minutes, greater than about 20 minutes, greater than about 25 minutes, greater than about 30 minutes, greater than about 1 hour, greater than about 2 hours, greater than about 3 hours, greater than about 4 hours, greater than about 5 hours, greater than about 10 hours, greater than about 24 hours, or greater than about 48 hours. In some embodiments, the exposing step is done for less than 48 hours, less than 24 hours, less than 10 hours, less than five hours, less than about 4 hours, less than about 3 hours, less than about 2 hours, less than about 1 hour, less than about 30 minutes, less than about 25 minutes, less than about 20 minutes, less than about 15 minutes, or less than about 10 minutes. Combinations of the above referenced ranges are also possible (e.g., the exposing step is done for greater than 25 minutes and less than 1 hour).

In some embodiments, the sequestration occurs as the protein/support composition is exposed to the sample comprising the plurality of first type of metal ion and the plurality of a second type of metal ion. According to certain embodiments, as the protein/support composition is exposed to the sample comprising the plurality of a first type of metal ion and the plurality of a second type of metal ion, the protein/support composition interacts with the plurality of a first type of metal ion and selectively sequesters at least a portion of the plurality of a first type of metal ion. Amounts of the plurality of metal ions sequestered will be described herein in further detail.

According to certain embodiments, the sequestration interaction between the protein/support composition and the plurality of a first type of metal ion and/or the plurality of a second type of metal ion can be any of a variety of suitable sequestration interactions understood by a person of ordinary skill in the art. For example, the protein/support composition may chelate the plurality of a first type of metal ion and/or the plurality of a second type of metal ion. As used herein, the term chelate generally refers to the multivalent binding of the first moiety (e.g., a metal) to a second moiety (e.g. a protein). In certain embodiments, upon exposure, the protein/support composition can covalently bind the plurality of a first type of metal ion and/or the plurality of a second type of metal ion. In some further embodiments, the protein/support composition and the plurality of a first type of metal ion and/or the plurality of a second type of metal ion interact in a host-guest interaction, a donor-acceptor interaction, or the like. Other embodiments of interactions are also possible.

According to certain embodiments, greater than about 90% of the plurality of a first type of metal ion in the sample is sequestered by the protein/support composition. The percentage of the plurality of the first type of metal ion in the sample that is sequestered by the protein/support composition can be calculated by comparing the mole percent of the first type of metal ion in the sample before and after sequestration. Any of a variety of suitable amounts of the plurality of a first type of metal ion may be sequestered by the protein/support composition. For example, in certain embodiments, greater than about 80%, greater than about 85%, greater than about 90%, greater than about 92%, greater than about 94%, greater than about 96%, greater than about 98%, greater than about 99%, greater than about 99.5%, or greater than about 99.8% of the plurality of a first type of metal ion in the sample is sequestered the protein/support composition. In some cases, the percentage of the plurality of a first type of metal ion that is sequestered by the protein/support composition is less than about 99.9%, less than about 99.8%, less than about 99.5%, less than about 99%, less than about 98%, less than about 96%, less than about 94%, less than about 92%, less than about 90%, less than about 85%. Combinations of the above-referenced ranges are also possible (e.g., greater than about 92% and less than about 99% of the plurality of a first type of metal ion that is sequestered by the protein/support composition).

In some embodiments, less than about 5% of the plurality of a second type of metal ion in the sample (and/or other pluralities of metal ions) is sequestered by the protein/support composition, according to certain embodiments. The percentage of the plurality of the second type of metal ion in the sample that is sequestered by the protein/support composition can be calculated by comparing the mole percent of the second type of metal ion in the sample before and after sequestration. Any of a variety of suitable amount of the plurality of a second type of metal ion in the sample may be sequestered the protein/support composition. For example, less than about 4.5%, less than about 4%, less than about 3.5%, less than about 3%, less than about 2.5%, less than about 2%, less than about 1.5%, less than about 1.0%, less than about 0.5%, or less than about 0.1% of the plurality of a second type of metal ion in the sample is sequestered by the protein/support composition. In certain cases, the percentage of the plurality of a second type of metal ion that is sequestered by the protein/support composition is greater than about 0.1%, greater than about 0.5%, greater than about 1.0%, greater than about 1.5%, greater than about 2%, greater than about 2.5%, greater than about 3%, greater than about 3.5%, greater than about 4%, or greater than about 4.5%. Combinations of the above-referenced ranges are also possible (e.g., greater than about 3% and less than about 4.5% of the plurality of a second type of metal ion in the sample is sequestered by the protein/support composition). These ranges also apply to any of the other types of metal ions that may be present in the samples. For example, less than about 5%, less than about 4.5%, less than about 4%, less than about 3.5%, less than about 3%, less than about 2.5%, less than about 2%, less than about 1.5%, less than about 1.0%, less than about 0.5%, or less than about 0.1% of the each of the other types of metal ions (e.g., not the first type of metal ion that is being selectively sequestered) is sequestered by the protein/support composition.

According to certain embodiments, the sequestration of the plurality of a first type of metal ion and the plurality of a second type of metal ion occurs simultaneously. For example, in some embodiments, the protein/support composition selectively sequesters greater than 90% of Zn(II) from a sample comprising Zn(II) and Cu(II), and also selectively sequesters less than 5% of Cu(II) from the sample comprising Zn(II) and Cu(II). Other metals are also possible for sequestration and described herein in further detail.

According to certain embodiments, the method of selectively sequestering metal ions is performed with the intention of selectively sequestering one metal at a time (e.g., sequestering greater than 90% of Zn(II) from a sample and less than 5% of Cu(II) from a sample comprising Zn(II) and Cu(II)).

In some embodiments, the metal ion-containing sample may contain more than two pluralities of metal ions (e.g., three, four, five, six pluralities of metal ions). According to certain embodiments, the sample may further comprise a plurality of a third type of metal ion and less than about 5% of the third type of metal ion in the sample is sequestered by the plurality of protein immobilized on a support. In certain embodiments, the sample may further comprise a plurality of a fourth type of metal ion, and less than about 5% of the fourth type of metal ion in the sample is sequestered by the plurality of protein immobilized on a support. According to some embodiments, the sample may further comprise a plurality of a fifth type of metal ion, and less than about 5% of the fifth type of metal ion in the sample is sequestered by the plurality of protein immobilized on a support. In some embodiments, the sample comprises at least about ten types of metal ions other than the first type of metal ion, and less than about 5% of each of the ten types of metal ions in the sample are sequestered by the plurality of protein immobilized on a support.

According to certain embodiments, the target metal to be sequestered from a metal ion-containing sample comprising multiple pluralities of metal ions (e.g., two, three, four, five, six different pluralities of metals) can be sequestered depending on the protein chosen that is immobilized on a support. For example, in a non-limiting embodiment, a plurality of S100A12 proteins immobilized on a NHS-modified agarose resin support can selectively sequester Zn(II) from a sample comprising Mg(II), Ca(II), Mn(II), Fe(II), Cu(II), and Zn(II). According to some embodiments, other proteins (e.g., other S100 proteins) can selectively sequester other pluralities of metals from samples comprising multiple pluralities of metals. More details are described herein explaining various embodiments of pluralities of protein molecules immobilized on a support for sequestration of various pluralities of metals.

Those of ordinary skill in the art will be aware of methods and techniques for determining the percentage of each type of metal ion sequestered following the exposure to the composition. For example, the amount of each type of metal ion present in the sample before and after exposure can be determined, and thus, the percentage change in the amount present before and after can be calculated.

In certain embodiments, the plurality of a first type of metal and the plurality of a second type of metal ion are quantified by any of a variety of suitable methods. One such example of a mass spectrometry method used to quantify the plurality of a first type of metal ion and the plurality of a second type of metal ion is inductively coupled plasma mass spectrometry (ICP-MS). Other methods of quantification of the plurality of a first type of metal ion and the plurality of a second type of metal ion include ICP-optical emission spectroscopy, atomic absorption spectroscopy, atomic emission spectroscopy, and the like.

Other embodiments described herein are related to a method of regenerating the protein/support composition (e.g., a plurality of protein molecules immobilized on a support) after sequestration of a plurality of a first type of metal ion. In certain embodiments, the method of regeneration comprises exposing the protein/support composition that has sequestered a plurality of a first type of metal ion (e.g., a plurality of protein molecules immobilized on a support and a first type of metal ions associated with the plurality of protein molecules, herein referred to as "the protein/support/metal composition") to a regeneration agent. According to certain embodiments, the regeneration step can be any of the aforementioned methods of exposure described herein.

According to certain embodiments, the regeneration agent is an acid. In certain cases, treatment of the protein/support/metal composition with a regeneration agent (e.g., an acid) lowers solution pH and releases the plurality of a first type of metal ion from the protein/support composition, providing a regenerated protein/support composition. According to certain embodiments, the release of the plurality of a first type of metal ion may comprise the breaking of a covalent bond between the plurality of protein molecules and the plurality of a first type of metal ion.

In some embodiments, the regeneration agent may be any of a variety of suitable chemicals that can alter the pH to a desired value to release metals. For example, in certain embodiments the regeneration agent is 1.0 M acetic acid (pH=3.8). Other suitable acids could include formic acid, propionic acid, butyric acid, valeric acid, caproic acid, oxalic acid, malic acid, citric acid, benzoic acid, carbonic acid, uric acid, hydrochloric acid and the like.

Figure 2:
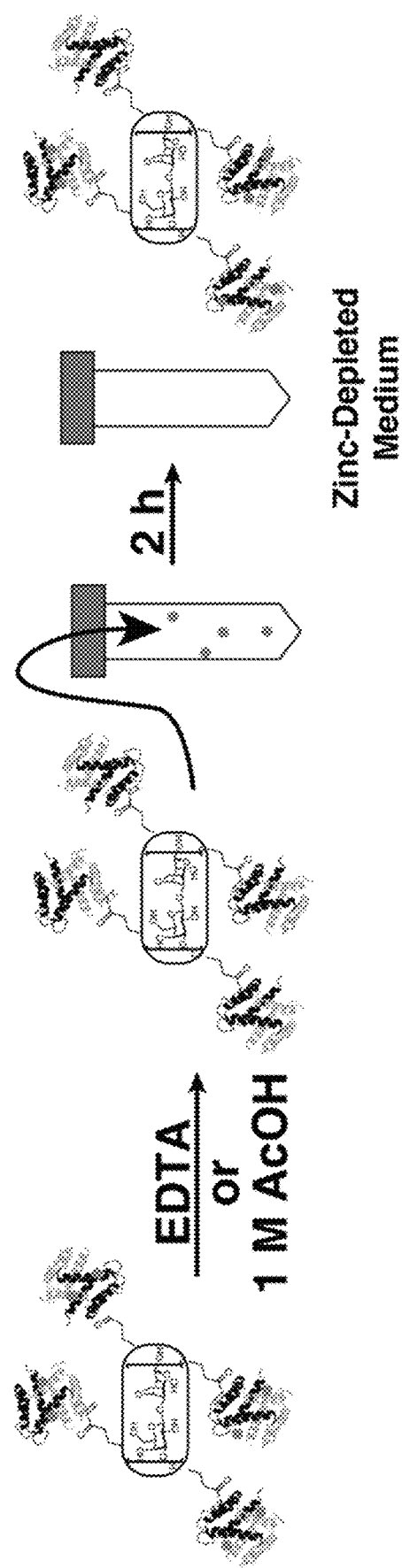
FIG. 2 shows, according to certain embodiments, an exemplary drawing where a plurality of protein molecules immobilized on a support and a first type of metal ion is exposed to one of two regeneration reagents: ethylenediamine tetraaceticacid (EDTA) or 1 M acetic acid.

In certain embodiments, the regeneration agent includes chelators such as ethylenediaminetetraacetic acid (EDTA). According to some embodiments, the protein/support/metal composition can be exposed to EDTA, such that EDTA will preferentially chelate the first type of metal ion associated with the protein/support composition. Upon chelation of the metal ions by EDTA, the protein/support composition will be regenerated and can be reused for sequestration of metals. FIG. 2 shows, according to certain embodiments, a drawing where a protein/support/metal composition is exposed to EDTA. For example, as shown in FIG. 2, in certain embodiments, the EDTA chelates the first type of metal ion associated with the protein/support composition, regenerating the protein/support composition. According to certain embodiments, the protein/support composition can then be reused to sequester metals from a metal ion-containing sample, reproducing the protein/support/metal composition. Other non-limiting examples of chelators include N,N,N',N'-tetrakis(2-pyridinylmethyl)-1,2-ethanediamine, nitrolotriacetic acid, and ethylene glycol-bis(2-aminoethylether)-N,N,N',N'-tetraaceticacid.

In some cases, the regeneration step comprises incubating the protein/support/metal composition with the regeneration agent. In certain other embodiments, the regeneration step comprises other methods known to a person of ordinary skill in the art, such as passing the regeneration agent over the protein/support/metal composition. In certain embodiments, for example, the protein/support/metal composition is set up in a chromatography column, and a solution comprising the regeneration agent is passed through the chromatography column comprising the protein/support/metal composition.

According to some embodiments, the regeneration step, comprising exposing the regeneration agent to the protein/support/metal composition can be done for any suitable amount of time. For example, the regeneration step is done for greater than about 5 minutes, greater than about 10 minutes, greater than about 15 minutes, greater than 20 minutes, greater than about 25 minutes, greater than about 30 minutes, greater than about 1 hour, greater than about 2 hours, greater than about 3 hours, greater than about 4 hours, greater than about 5 hours. In some embodiments, the regeneration step is done for less than about 4 hours, less than about 3 hours, less than about 2 hours, less than about 1 hour, less than about 30 minutes, less than about 25 minutes, less than about 20 minutes, less than about 15 minutes, or less than about 10 minutes. Combinations of the above referenced ranges are also possible (e.g., the regeneration step is done for greater than 25 minutes and less than 1 hour).

According to certain embodiments, following the regeneration step of exposing the protein/support/metal composition (e.g., a plurality of protein molecules immobilized on a support and a first type of metal ions associated with the plurality of protein molecules) to the regeneration agent (e.g. acetic acid), the protein/support composition retains the capacity to sequester at least 90% of a plurality of a first type of metal ion from a cell culture medium. For example, less than 5% of the plurality of a first type of metal ion remain associated with the protein/support composition following the regeneration step of exposing the protein/support/metal composition to a regeneration agent. The percentage of the plurality of a first type of metal ion associated with the protein support/composition following the regeneration step can be calculated by comparing the amount of the plurality of a first type of metal ion associated with the protein/support composition in the sample directly after sequestration (and before exposure to a regeneration agent) to the amount of the plurality of a first type of metal ion associated with the protein/support composition after exposure to the regeneration agent (i.e., the percentage corresponds to the mole percent of the plurality of the first type of metal ion still associated with the protein/support composition in comparison to the mole percent of the plurality of the first type of metal ion associated with the protein/support composition directly after sequestration).

According to certain embodiments, the percentage of the plurality of a first type of metal ions still associated with the protein/support composition after exposure to a regeneration agent is less than about 4.5%, less than about 4%, less than about 3.5%, less than about 3%, less than about 2.5%, less than about 2%, less than about 1.5%, less than about 1.0%, or less than about 0.5%. According to some aspects, the percentage of the plurality of a first type of metal ion associated with the protein/support composition after exposure to a regeneration agent is greater than about 0.1%, greater than about 0.5%, greater than about 1.0%, greater than about 1.5%, greater than about 2%, greater than about 2.5%, greater than about 3%, greater than about 3.5%, or greater than about 4%. Combinations of the above referenced ranges are also possible (e.g., greater than 2% and less than 3% of the plurality of a first type of metal ions are associated with the protein/support composition after exposure to a regeneration agent).

According to certain embodiments, regeneration of a selective metal-ion chelating resin can be repeated multiple times. According to some embodiments, the method of regenerating a selective metal ion sequestration agent is repeated five times. The method of regenerating a selective metal ion sequester can be repeated any of a variety of suitable number of times. For example, the method of regenerating a selective metal ion sequestration agent is repeated one, two, three, four, five, ten, fifteen, twenty, fifty, one hundred times, etc.

In certain embodiments, after regeneration of protein/support composition, the percent amount of the plurality of a first type of metal ion sequestered during another exposing step may not change significantly (e.g., change by less than 5%). For example, according to certain embodiments, after multiple regenerations cycles of the protein/support composition (e.g., two, five, twenty, fifty, one hundred regeneration cycles), any of a variety of suitable amounts of the plurality of a first type of metal ion in a sample may be sequestered by the protein/support composition. For example, the amount of the plurality of a first type of metal ion sequestered after multiple regeneration cycles (e.g., four, ten, etc.) is greater than about 85%, greater than about 90%, greater than about 95%, greater than about 98%, greater than about 99%, or greater than about 99.5%. In some cases, the percentage of the plurality of a first type of metal ion that is sequestered after multiple regeneration cycles (e.g., four, ten, etc.) is less than about 99.9%, less than about 99.5%, less than about 99%, less than about 98%, less than about 95%, or less than about 90%. Combinations of the above-referenced ranges are also possible (e.g., greater than about 87% and less than about 99% of the plurality of a first type of metal ion is sequestered by the protein/support composition).

According to some embodiments, after regeneration of the protein/support composition, the percent amount of the plurality of a second type of metal ion sequestered may not change significantly (e.g., less than 5%). For example, according to certain embodiments, after multiple regenerations cycles of the protein/support composition (e.g., two, five, twenty, fifty, one hundred regeneration cycles), any of a variety of suitable amounts of the plurality of a second type of metal ion in a sample may be sequestered by the protein/support composition. For example, the amount of the plurality of a second type of metal ion sequestered after multiple regeneration cycles (e.g., four, ten, etc.) is less than about 7.5%, less than about 6%, less than about 4%, less than about 3%, less than about 2%, less than about 1.5%, less than about 1%, or less than about 0.5%. In certain cases, the percentage of the plurality of a second type of metal ion that is sequestered by the protein/support composition after multiple regeneration cycles (e.g., four, ten, etc.) is greater than about 0.1%, greater than about 0.5%, greater than about 1%, greater than about 1.5%, greater than about 2%, greater than about 3%, greater than about 4%, or greater than about 6%. Combinations of the above-referenced ranges are also possible (e.g., greater than about 0.5% and less than about 6% of the plurality of a second type of metal ion is sequestered by the protein/support composition after multiple regeneration cycles).

The method of regeneration is useful, according to certain embodiments, because the protein/support composition can be used multiple times to sequester metal ions from a sample (e.g., a biological sample). According to certain embodiments, the protein/support composition can be used to sequester a plurality of metal ions from a metal ion-containing sample, followed by repletion of the sequestered metals in that sample. Repletion, according to certain embodiments, can be done with a radioisotope of the depleted metal or with a defined, non-natural, isotopic composition of to enable a variety of studies.

According to certain embodiments, any of a variety suitable amounts of the protein/support composition can be used for the methods of sequestration and/or regeneration. For example, greater than about 1 mg/mL, greater than about 5 mg/mL, greater than about 10 mg/mL, greater than about 20 mg/mL, is used for the methods of sequestration and/or regeneration. According to certain embodiments, less than about 20 mg/mL, less than about 10 mg/mL, or less than about 5 mg/mL of the protein/support composition can be used for the methods of sequestration and/or regeneration.

According to certain embodiments, the protein/support composition can be present in an aqueous solution. According to certain embodiments, the solution comprising a plurality of protein molecules can be buffered (e.g., tris buffer, PBS buffer). In certain embodiments, the solution comprising a plurality of protein molecules can have any of a variety of suitable pH values. For example, the pH of the solution comprising a plurality of protein molecules is greater than about 3.0, greater than about 3.5, greater than about 4.0, greater than about 4.5, greater than about 5.0, greater than about 5.5, greater than about 6.0, greater than about 6.5, greater than about 7.0, greater than about 7.5, greater than about 8.0, greater than about 8.5, greater than about 9.0, greater than about 9.5, greater than about 10.0. According to certain embodiments, the pH of the solution comprising a plurality of protein molecules is less than about 10.0, less than about 9.5, less than about 9.0, less than about 8.5, less than about 8.0, less than about 7.5, less than about 7.0, less than about 6.5, less than about 6.0, less than about 5.5, less than about 5.0, less than about 4.5, less than about 4.0, less than about 3.5, less than about 3.0. Combinations of these ranges are also possible (e.g., the pH of the solution comprising a plurality of protein molecules in solution is less than 6.0 but greater than 4.5). In some embodiments, the solution may be at physiological pH. According to certain embodiments, the pH of the solution will change after coming into contact with a regeneration agent (e.g., an acid). In certain embodiments, the plurality of protein molecules dissolved in solution includes an additive (e.g., such as an electrolyte). In certain embodiments, the electrolyte dissolved in solution is a sodium salt (e.g., NaCl).

According to some embodiments, the sample comprising the plurality of a first type of metal ion and the plurality of a second type of metal ion is a biological medium. In some embodiments, this biological medium is cell culture medium. In certain embodiments, the sample comprising a plurality of a first type of metal ion and a plurality of a second type of metal ion is mammalian serum. According to certain embodiments, the sample comprising a plurality of a first type of metal ion and a plurality of a second type of metal ion is human serum. In some certain embodiments, the cell culture medium comprises a plurality of a first type of metal ion, a plurality of a second type of metal ion, and other pluralities of metal ions (e.g., a third plurality, a fourth plurality, a fifth plurality, a tenth plurality, a twentieth plurality etc.). In some cases, the cell culture medium is a microbial growth medium. According to certain embodiments, the cell culture medium is a mammalian cell culture medium. Specific examples of cell culture mediums include Minimal Essential Medium/Fetal Bovine Serum (MEM/FBS), Dulbecco's Modified Eagle Medium/Fetal Bovine Serum (DMEM/FBS), Roswell Park Memorial Institute medium/Fetal Bovine Serum (RPMI/FBS), McCoy's 5A medium/Fetal Bovine Serum (McCoy's 5A/FBS), Ham's F-12K meidum/Fetal Bovine Serum (Ham's F-12K/FBS), Dulbecco's Modified Eagle Medium/Nu-Serum (DMEM/Nu-Serum), Roswell Park Memorial Institute medium/Nu-Serum (RPMI/Nu-Serum), Opti-MEM Reduced-Serum medium, and the like.

According to some embodiments, the solution to be depleted of a metal is human serum.

According to other embodiments, metal ions in a sample comprising the plurality of a first type of metal ion and the plurality of a second type of metal ion may be a series of divalent metal coordination complexes. Metal ions in the sample may be from contaminated water sources, vehicle emissions, batteries, paints, aged infrastructure, and the like. Other sources of metal ion-containing samples are also possible.

According to certain embodiments, the plurality of a first type of metal ion and the plurality of a second type of metal ion may be two different types of metal ions (i.e., not the same). The sample comprising the plurality of a first type of metal ion and a plurality of a second type of metal ion may be a mixture of metals. For example, the sample may comprise more than two (e.g., three, four, five, ten, twenty, etc.) pluralities of metals. According to certain embodiments, both the plurality of a first type of metal and the plurality of a second type of metal ion may be any d-block metal on the periodic table (e.g., the transition metals from columns 3 through 12). Both the plurality of a first type of metal and the plurality of a second type of metal ion may be any first-row transition metal (e.g., row four on the periodic table). Specifically, the plurality of a first type of metal and the plurality of a second type of metal ion may be Sc, Ti, V, Cr, Mn, Fe, Co, Ni, Cu, Zn, and the like. In some further embodiments, the plurality of a first type of metal ion and the plurality of a second type of metal ion may comprise heavy metals, lanthanides, actinides, and the like.

According to certain embodiments, the compositions and methods described herein have important applications and uses. For example, in some embodiments, the method of selectively sequestering metal ions comprising exposing the protein/support composition to a sample comprising metal ions is important for perturbing metals in biological settings. In certain embodiments, the methods described herein can be used in order to precisely interrogate the consequences of dysregulated metals in complex settings. Specifically, selective sequestration of metal ions from sources of metals such as cell culture medium enables the study of metal deficiencies in metazoan cells. Furthermore, it is also relevant to note that according to certain embodiments, the compositions and methods described herein are straightforward and easy to use.

The following examples are intended to illustrate certain embodiments of the present invention, but do not exemplify the full scope of the invention.

Example 1

This example first describes proof of principle experiments for the use of S100A12 to deplete mammalian cell culture medium of zinc followed by use of a plurality of molecules of the protein immobilized on a support to sequester zinc from other, more complex, mammalian cell culture media.

Figure 3:
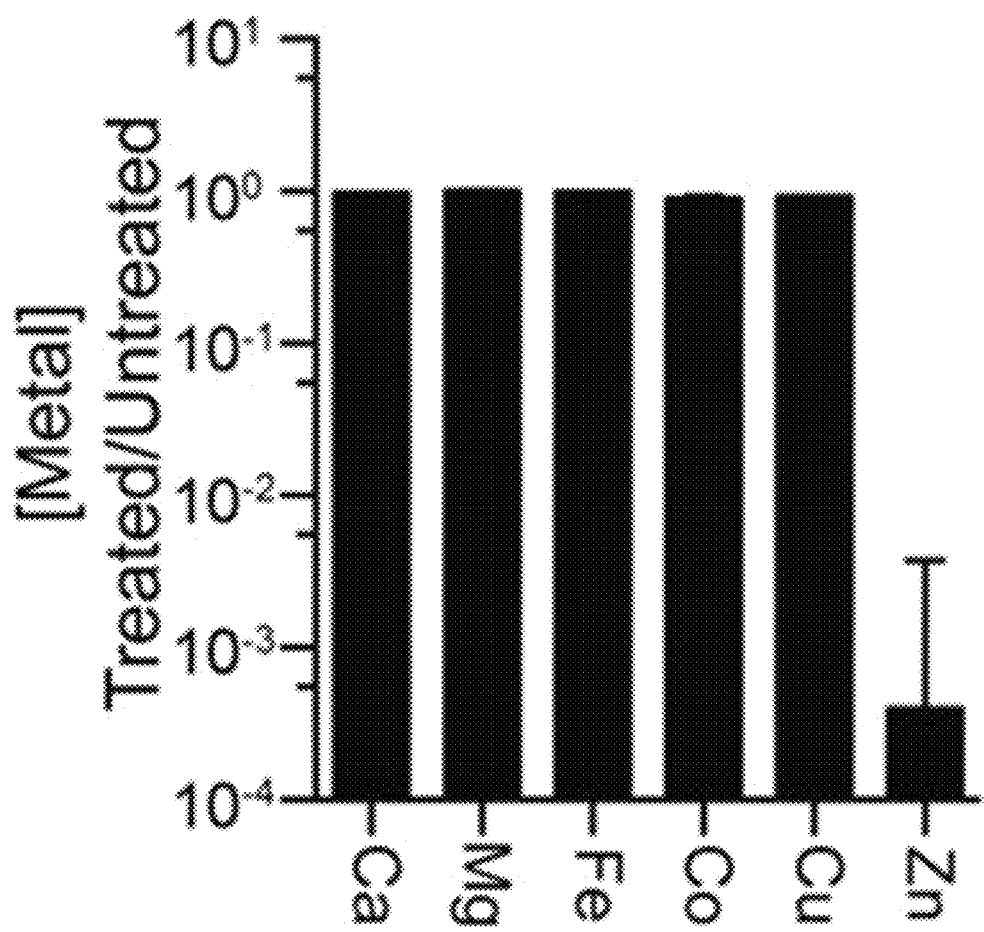
FIG. 3 shows, according to some embodiments, inductively coupled plasma mass spectrometry (ICP-MS) analysis indicating that a source of metal ions is depleted of Zn(II) by addition of S100A12 to the medium followed by removal of the protein with a 10 kD molecular weight cutoff filter.

First, recombinant S100A12 was examined for its capacity to deplete Zn(II) from the chemically-defined protein-free Freestyle™ mammalian cell culture medium. Briefly, 25 μM S100A12 was incubated with Freestyle™ medium for four hours prior to filtering the S100A12-containing medium through a 10-kDa molecular weight cutoff filter to remove the protein. ICP-MS measurement of the metal ion concentrations in untreated versus S100A12-treated medium revealed that S100A12 selectively depletes Freestyle™ medium of 99% of total Zn(II) (FIG. 3).

Motivated by the selectivity of S100A12 for Zn(II) in a simple mammalian cell culture medium, the ability of S100A12 to deplete Zn(II) more commonly used medium formulations that contain high concentrations of protein or fetal bovine serum (FBS) was evaluated. The method described above, which involved separation of Zn(II)-bound S100A12 from treated complex medium formulations using a molecular weight cutoff filter would deplete high-molecular-weight biomolecules present in medium, and thereby perturb the composition of the medium.

Figure 4:
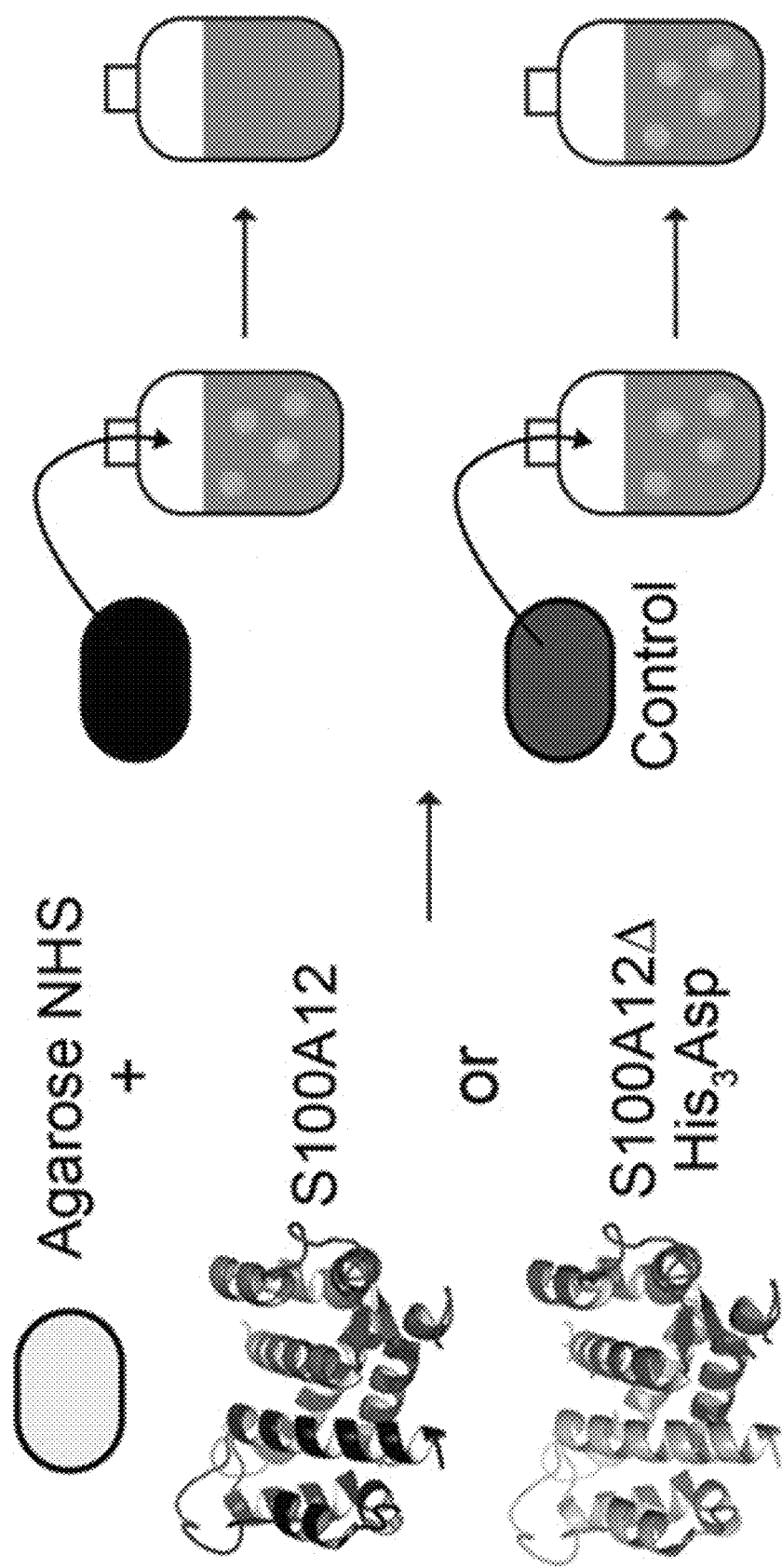
FIG. 4 shows, according to certain embodiments, a non-limiting example of a plurality of proteins immobilized on a support that specifically sequesters metal ions, and a control the specifically does not sequester metal ions.
Figure 5:
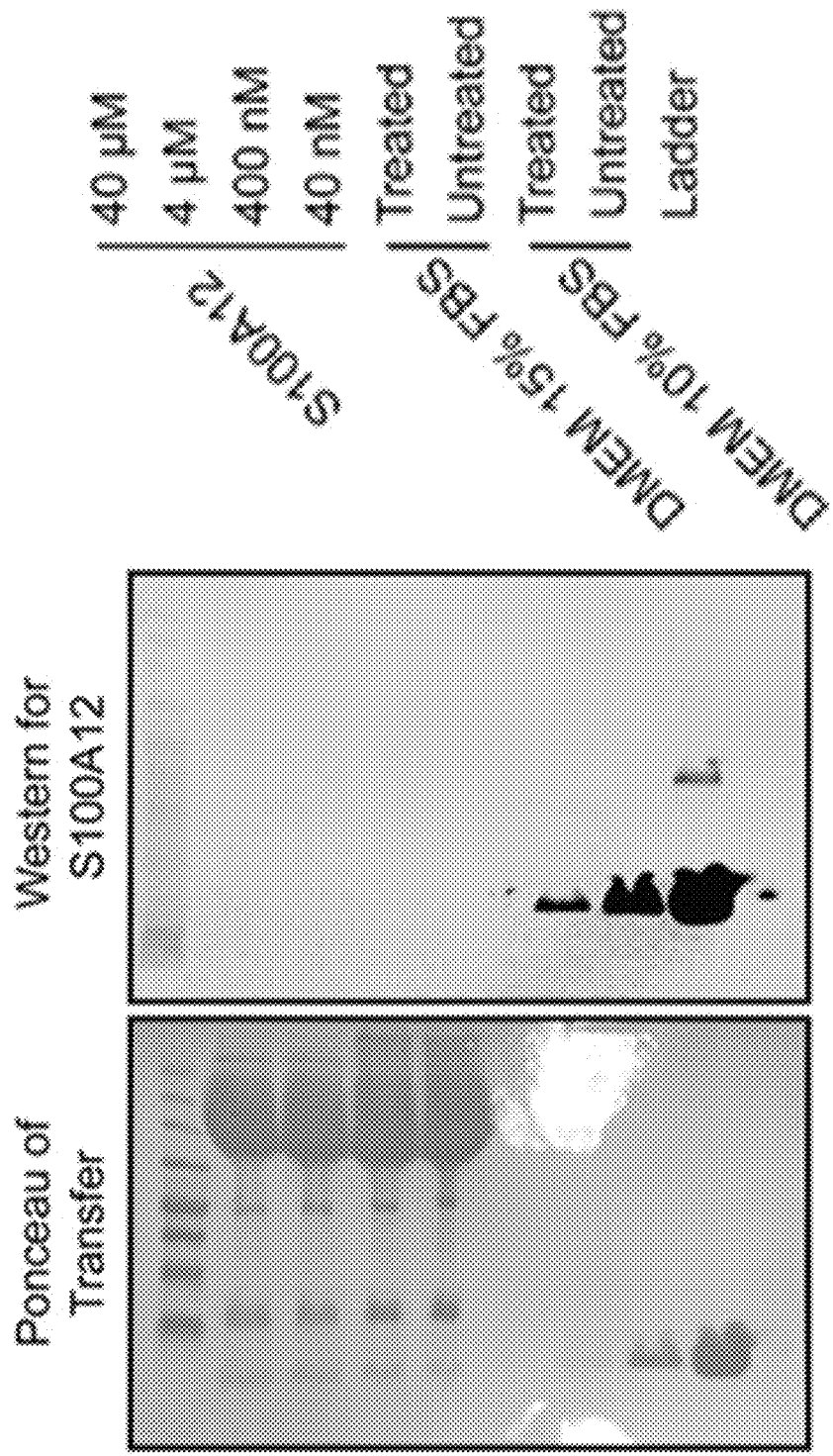
FIG. 5 shows, in accordance with certain embodiments, a Western blot analysis of treated source of metal ions in order to demonstrate that immobilized protein does not leach into metal-depleted medium.

Covalent immobilization of S100A12 on a solid support allows for chelation of Zn(II) by the protein and facile removal of Zn(II)-bound S100A12 from any cell culture medium. DMEM/FBS was treated with S100A12 conjugated to agarose (FIG. 4), and ICP-MS analysis indicated that >99% of Zn(II) from the medium was specifically sequestered. Moreover, Western blot analysis of treated DMEM/FBS using an anti-S100A12 antibody indicated that a detectable quantity of protein did not leach from the resin, as shown in FIG. 5. Considering that metal-ion binding by S100A12 requires dimerization/oligomerization of the protein, it is remarkable that that covalent, nonspecific, immobilization of S100A12 does not prevent metal binding.

Figure 6:
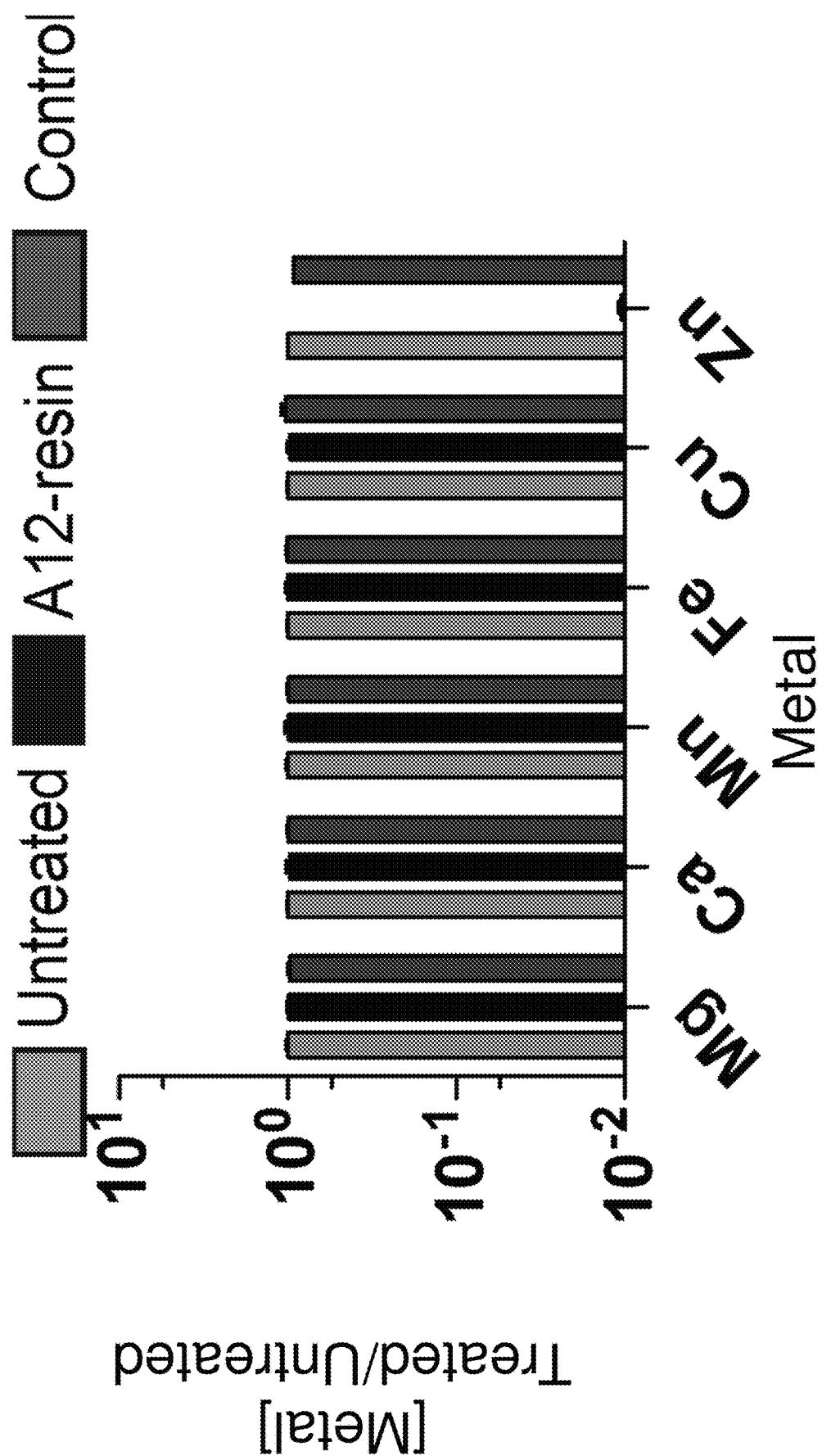
FIG. 6 shows, according to certain embodiments, a plot of the ratio of the treated to untreated metal concentration in mammalian cell culture medium (DMEM/FBS) depleted, by treatment with a plurality of protein molecules immobilized on a support, of Zn(II) but not significantly depleted of any other biologically relevant metals after and before.

A control resin was prepared by conjugating S100A12ΔHis$_3$Asp, a variant of S100A12 that lacks the His$_3$Asp Zn(II)-binding sites, to agarose. Treatment of DMEM/FBS with the control resin (FIG. 4) does not significantly change the concentration of Zn(II) or other metal ions (FIG. 6).

Figure 7:
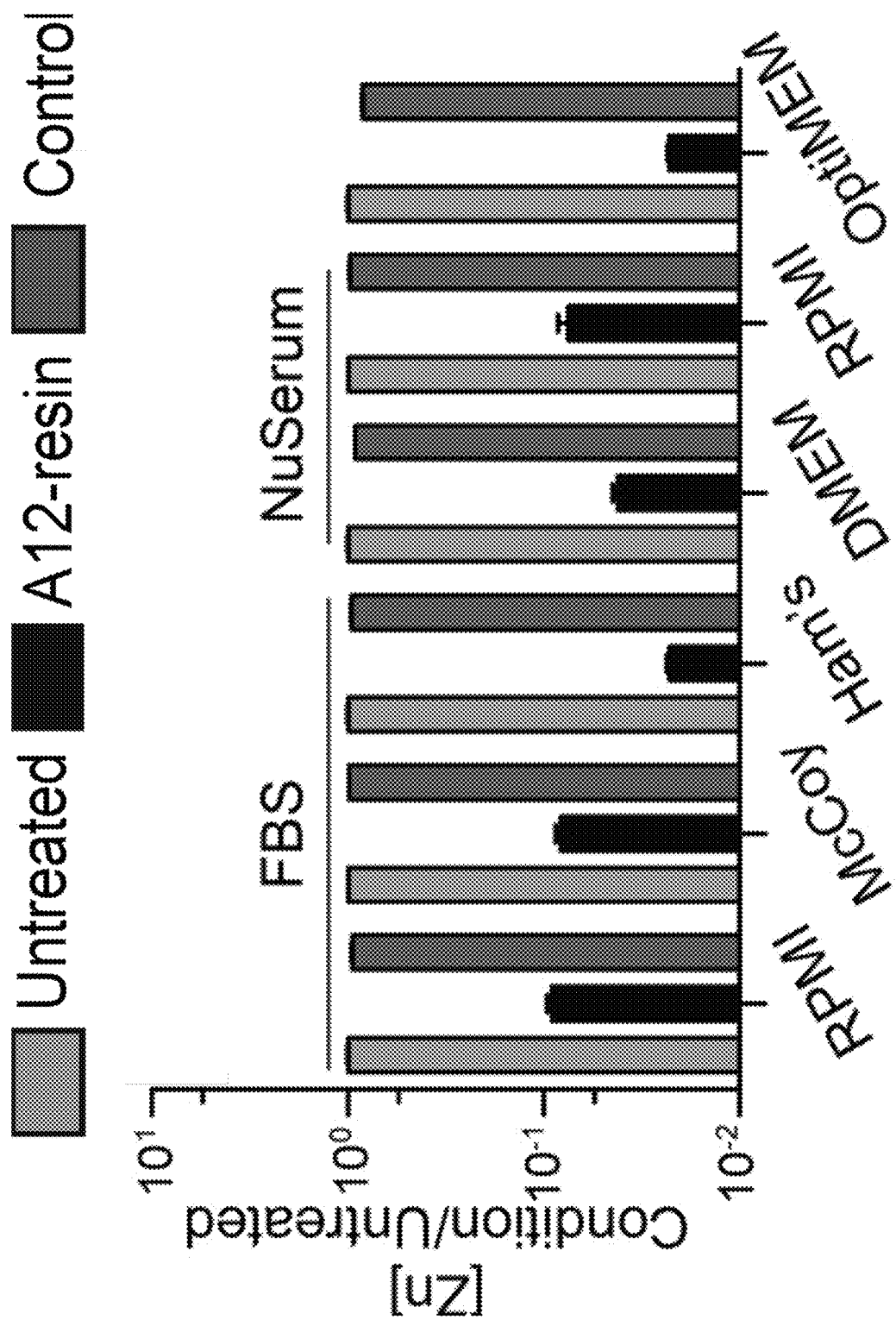
FIG. 7 shows, in certain embodiments, a plurality of protein molecules immobilized on a support that depletes Zn(II) from an array of diverse cell culture medium formulations.

The immobilized protein resin was then tested against six additional complex media formulations including RPMI/FBS, McCoy's 5A/FBS, Ham's F-12K/FBS, DMEM/NuSerum™, RPMI/NuSerum™, and OptiMEM™. The S100A12-agarose immobilized protein resin selectively depleted Zn(II) from all the diverse media (FIG. 7).

Figure 8:
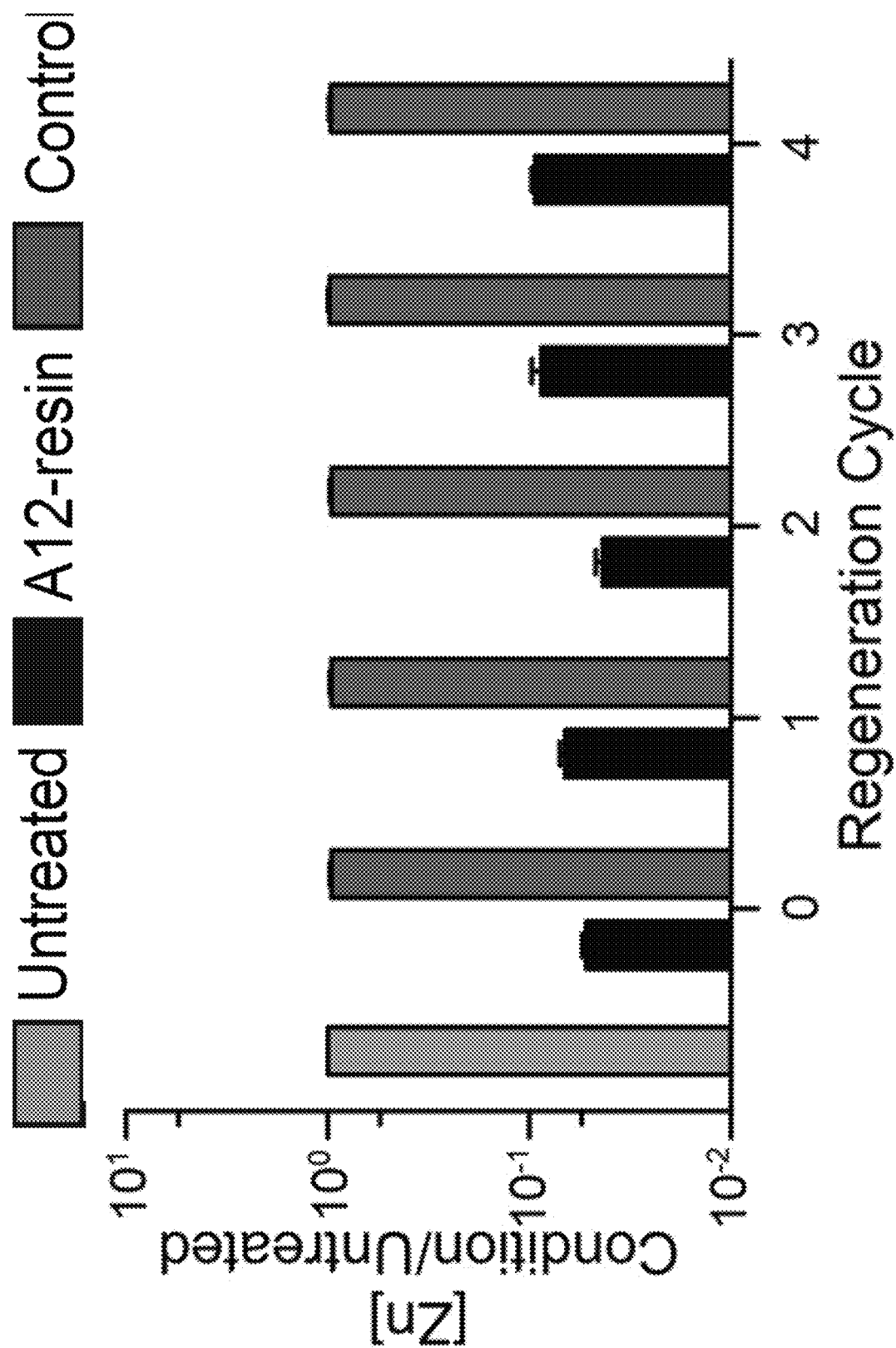
FIG. 8 shows, according to some embodiments, that regeneration of a plurality of protein molecules immobilized on a support enables repeated use of such material.

The S100A12-agarose immobilized protein resin can deplete a range of biological media and is regenerable. After depleting DMEM/FBS of Zn(II) with the S100A12-agarose immobilized protein resin, the recovered resin was treated with 1.0 M acetic acid (pH=3.8) for 15 minutes, and then washed with PBS and DMEM to neutralize the pH of the resin suspension. Remarkably, the protein retained its Zn(II)-binding capacity through this harsh treatment. The protocol yielded a refreshed S100A12-agarose immobilized protein resin that removed Zn(II) from subsequent batches of medium. The method of recycling can be repeated with negligible loss of Zn(II) removal efficacy, as shown in FIG. 8.

Example 2

This example describes the investigation of the response of cells to growth in Zn(II)-depleted and Zn(II)-repleted medium. The data herein are presented as evidence of the Zn(II)-selectivity of S100A12 immobilized on agarose because all phenotypes of cells grown in Zn(II)-depleted medium were entirely rescued by culture of cells in Zn(II)-repleted medium.

Figure 9:
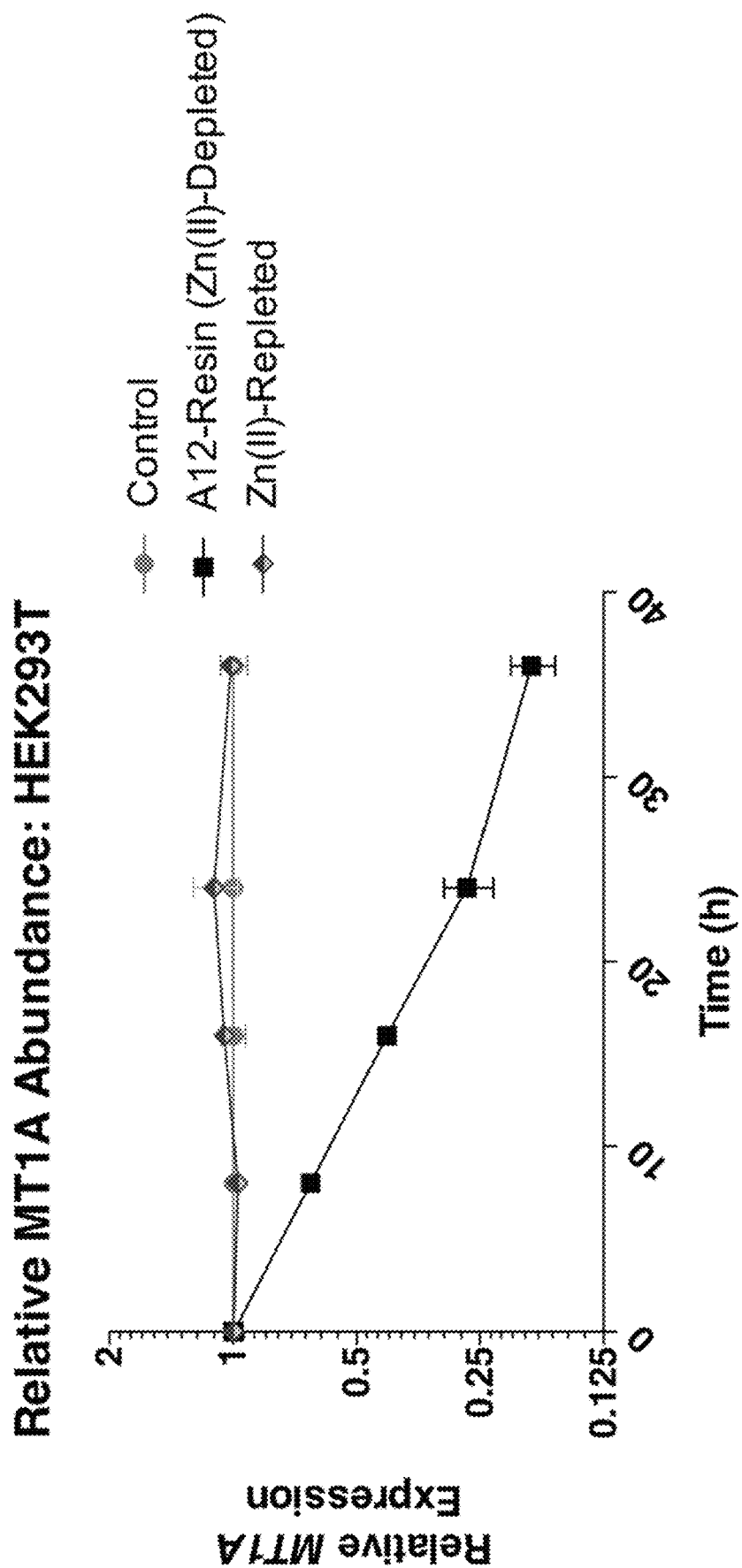
FIG. 9 shows, in some embodiments, cells cultured in a Zn(II)-depleted medium that exhibit a loss of metabolic activity as analyzed over 4 days of culture.

Metabolic activity of HEK293T cells cultured in Zn(II)-depleted medium decreased significantly after 2 days of culture compared to control. This metabolic defected is demonstrated both by resazurin assay (FIG. 9). Zn(II) repletion rescues the observed metabolic defects.

Figure 10:
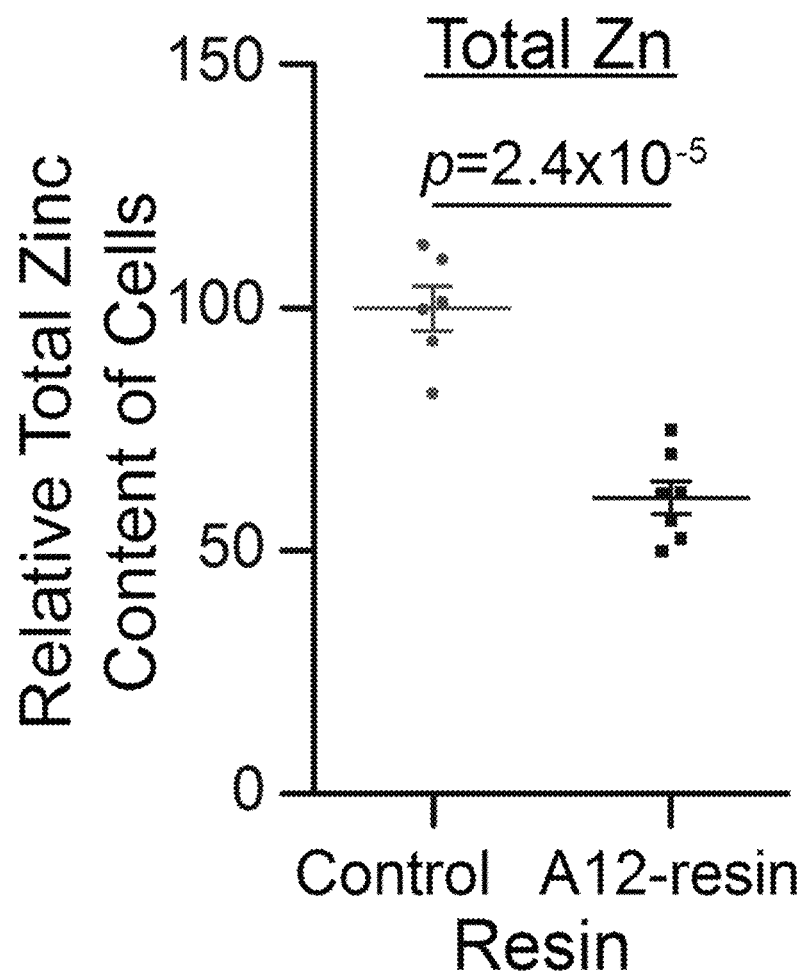
FIG. 10 shows, according to certain embodiments, a plot showing that the total cellular Zn(II) content of cells cultured in Zn(II)-depleted medium is diminished relative to cells cultured in Zn(II)-adequate medium.

Next, the transcriptional response of HEK293T cells to Zn(II) deficiency was investigated. HEK293T cells cultured in Zn(II)-depleted medium exhibit a decrease in metallothionein transcript abundance in response to Zn(II) deficiency (FIG. 10). This decrease is an established hallmark of Zn(II) starvation.

The metallomic consequences for HEK293T cells cultured in S100A12-agarose immobilized protein resin treated DMEM/FBS were also assessed. The total cellular Zn(II) change was calculated as a consequence of 1 day of growth in Zn(II)-depleted medium. Culture in Zn(II)-depleted medium decreases total cellular Zn(II) compared to control cells by ~40%, as shown in FIG. 10 The total concentrations of other metals were unperturbed by culture in Zn(II)-depleted medium.

Figure 11:
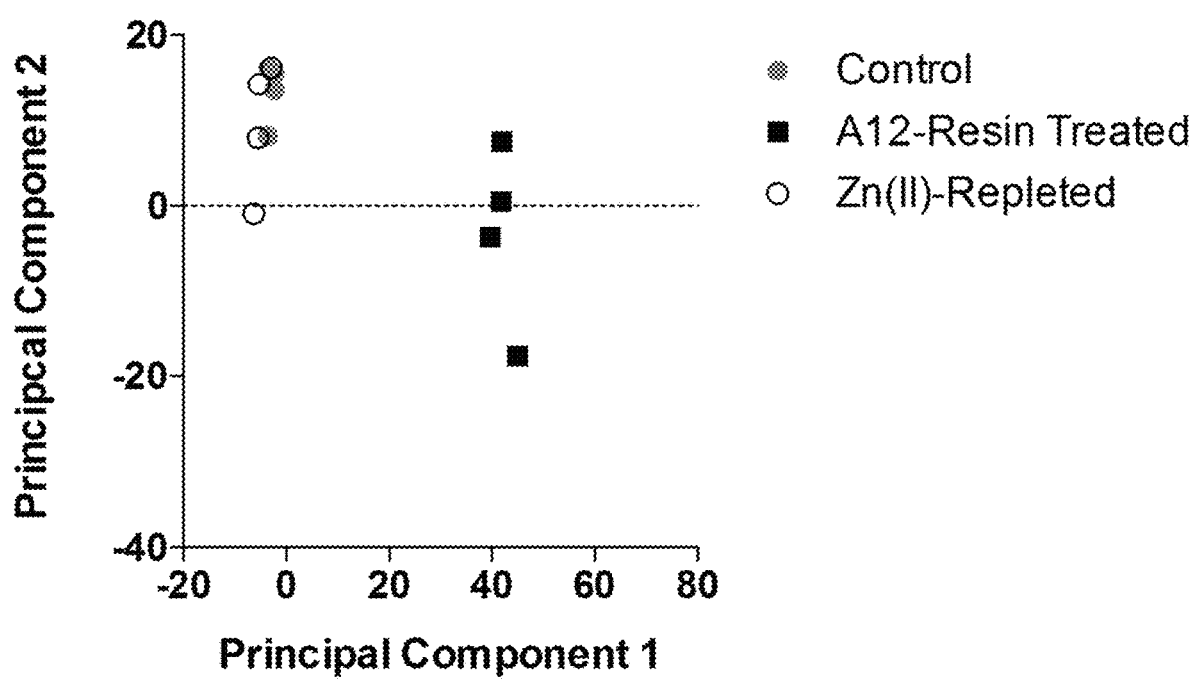
FIG. 11 shows, according to certain embodiments, a principal component analysis demonstrating that HEK293T cells cultured in Zn(II)-depleted medium for 24 are distinguished on principal component 1 from cells cultured in control-treated or repleted medium.

Finally, RNA-Seq was performed to globally assess the response of HEK293T cells to culture in Zn(II)-depleted medium. Principal component analysis revealed that the transcriptomes of HEK293T cells cultured in Zn(II)-depleted medium for 24 h are distinguished on principal component 1 from cells cultured in control or Zn(II)-repleted medium (FIG. 11). These data indicate that Zn(II) starvation principally contributes to the transcriptomic differences between these cell populations and, by extension, that A12-resin selectively depletes Zn(II) from cell culture medium.

Example 3

This example describes the protocol for the purification of S100A12.

S100A12 in a pet41a plasmid was obtained and BL21 (DE3) inoculated into an overnight culture containing kanamycin sulfate (50 µg/L). The next morning, the overnight culture was diluted (1:100) into 2 L of LB containing kanamycin sulfate (50 µg/L) in a 4 L baffled flask maintained in a shaking incubator (150 RPM) at 37° C.

When the $OD_{600}$ of the culture reached 0.6 (typically 1-2 hours after addition of overnight culture), freshly prepared IPTG (1 mL of 0.5 M stock diluted to a final concentration of 250 µM) was added to the 2 L culture. 4 hours later the culture was collected by centrifugation (8,000 RPM, JA10 rotor, 4° C., 10 min) and scraped into a 50 mL falcon tube. The paste was pelleted by brief centrifugation at 3,000 RPM in a benchtop centrifuge and the resulting pellet was frozen in liquid nitrogen then stored at −80° C. Pellets typically had a volume of 4-5 mL.

A pellet of S100A12 was thawed on ice for 1-3 hours before being resuspended in lysis buffer (50 mM Tris (pH 8.0), 100 mM NaCl, 1 mM EDTA, 1 mM PMSF, 0.5% Triton X-100; 50 mL). The suspension was homogenized (dounce homogenizer) before sonication (30% amplitude, 2:30 total time, 30 sec on, 10 sec off, no microtip). The sonicated lysate was pelleted to afford soluble and insoluble fractions (16,000 RPM, JA25.5 rotor, 4° C., 10 minutes). The soluble fraction was decanted and stored at 4° C. The insoluble portion was resuspended, homogenized, and sonicated as above, before being subjected to another round of centrifugation (16,000 RPM, JA25.50 rotor, 4° C., 10 minutes). The second soluble portion was combined with the first soluble portion. Next, ammonium sulfate (37.5 g) was added over 15 minutes to gently stirring soluble lysate at 4° C. Stirring was continued at 4° C. for 1-3 hours. Lysate was centrifuged (16,000 RPM, JA25.5 rotor, 4° C., 10 minutes), decanted into a clean plastic beaker, then added to a dialysis bag (3,500 Da molecular weight cutoff) and dialyzed against MonoQ Buffer A (20 mM HEPES, pH=8.0) at 4° C. The dialysis buffer was changed a minimum of four times with at least 12 h between each change.

All buffers were prepared with Milli-Q water with a resistivity of 18.2 mΩ×cm and filtered through a 0.22 µM bottle top filter (VWR) prior to chromatography. Prior to first use, all columns were washed with EDTA (500 µM, 2 Column Volumes (CV) for MonoQ, 100 mL for S75) then with water.

The MonoQ column was washed immediately prior to use with 2 CV 20 mM HEPES pH=8.0 (MonoQ A), 2 CV 20 mM HEPES (pH=8.0) and 1.0 M NaCl (MonoQ B), 2 CV MonoQ A, 2 CV MonoQ B, 2 CV MonoQ A at 2-4 mL/minute. After every protein preparation, the column was washed with 2 CV 2 M NaCl, 2 CV 2 M NaOH, 4 CV 2M NaCl, and then finally 4 CV MonoQ A, according to the manufacturer's instructions. Whenever pressure increases were observed, the column was washed with 6 M guanidinium hydrochloride to elute strongly bound proteins.

The S75 column was washed with 100 mL of water, 100 mL 1 M NaOH, 100 mL water, before pre-equilibration with either 450 mL 20 mM Tris (pH=7.5)+100 mM NaCl+ or 450 mL of Corning PBS (10 mM $NaH_2PO_4$, 1.8 mM $KH_2PO_4$ (137 mM NaCl, 2.7 mM KCl,).

Prior to FPLC purification, lysate was filtered through a 0.2 µm bottle top filter into a 250 mL plastic bottle. 30-50 mL of lysate was loaded through the A line of the FPLC at a rate of 2 mL/minute. After the sample was loaded the column was washed with MonoQ A (9 CV, 2 mL/min) the protein was eluted in 10% MonoQ B (8 CV, 2 mL/min), 50% B (7 CV, 50% B), and finally 100% B (6 CV, 2 mL/min). MonoQ runs were repeated until all lysate was purified. bFractions that eluted at 10% MonoQ B were pooled and concentrated with a 10 kD MWCO filter to a volume of less than 10 mL. After filtration through a 0.2 µm filter (regenerated cellulose, VWR 28145-477), the partially purified lysate was then loaded onto an S75 column, either by direct addition onto the column with a syringe or through the A line of the FPLC. Protein was eluted with isocratic flow of 1.4 CV of either 100 mM NaCl+20 mM Tris pH=7.5 or PBS. Typical yields for S100A12 were between 100 and 200 mg/2 L of bacterial culture. Yields of S100A12ΔHis$_3$Asp, the metal-binding site null variant of S100A12, varied more widely (between 30 and 120 mg/2 L bacterial culture). The purity of each protein was assessed by gel electrophoresis (15% gel, 100V, 100 min). The identity of each protein was verified with MALDI (Matrix: sinapinic acid).

Protein concentration was measured using a Take3 plate reader based on the predicted extinction coefficient of the S100A12 dimer (5960 M$^{-1}$ cm$^{-1}$) and a path length of 0.048 cm.

Example 4

This example describes the preparation of the S100A12-agarose immobilized protein resin. As demonstrated in example 1, treatment of mammalian cell culture medium with this resin selectively depletes Zn(II) from the medium.

S100A12 or S100A12ΔHis$_3$Asp (5 mg/mL in PBS) was incubated with NHS agarose (75 mg/mL protein solution) for 2 hours at room temperature in a BioRad protein purification column (731-1550). This resin to protein ratio was chosen because at this ratio all input protein bound to the resin. After 2 hours, the supernatant was eluted from the column and the resin was quenched with Tris (1.0 M pH=7.5) for 30 minutes. Subsequently, the resin was washed three times with 10 mL of PBS, then incubated with acetic acid (pH=3.8, 1 mL/mL resin) for 30 minutes before being washed thoroughly with PBS, then DMEM containing phenol red (no FBS) until the DMEM no longer eluted as a yellow solution. Finally, the resin was washed with 5 mL PBS per mL resin.

The resin was washed with PBS before being suspended in acetic acid (1 M, pH=3.8, 1 mL/0.2 mL dry resin) for 10 minutes. The resin was then washed with PBS (10 mL) before being washed with phenol red-containing DMEM (10 mL; [Zn] in DMEM is approximately 18 ppb) until the DMEM turned red, which indicates the pH of the DMEM is greater than 6.8. The resin was then washed with PBS before being reapplied to deplete a solution of Zn(II).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
a plurality of S100 protein molecules; and
a support comprising a plurality of functional groups,
wherein the plurality of S100 protein molecules are covalently immobilized on the support via reactions between the plurality of functional groups and amine groups of the plurality of S100 protein molecules, such that the covalently immobilized S100 protein molecules have binding sites available for chelation of metal ions and are thus configured to selectively sequester metal ions.

2. The composition of claim 1, wherein the plurality of S100 protein molecules is a plurality of S100A12 protein molecules.

3. The composition of claim 1, wherein the support is a solid support.

4. The composition of claim 1, wherein the support is agarose resin.

5. The composition of claim 4, wherein the agarose resin is N-hydroxy-succinimide-modified agarose resin.

6. The composition of claim 1, wherein the plurality of S100 protein molecules is covalently attached to the support through amide linkages.

7. The composition of claim 1, wherein the functional groups are ester groups.

8. The composition of claim 1, wherein selectively sequestering metal ions comprises:
exposing the composition to a sample comprising a plurality of a first type of metal ion and a plurality of a second type of metal ion;
wherein following the exposing step, greater than about 90% of the first type of metal ion in the sample are sequestered by the plurality of S100 protein molecules immobilized on the support, and;
less than about 5% of the second type of metal ion in the sample are sequestered by the plurality of S100 protein molecules immobilized on the support.

9. A composition, comprising:
a plurality of S100 protein molecules; and
a support comprising a plurality of functional groups,
wherein the plurality of S100 protein molecules are covalently immobilized on the support via reactions between the plurality of functional groups and amine groups of the plurality of S100 protein molecules,
whereby the covalently immobilized protein molecules have more binding sites available for chelation of metal ions than an essentially identical comparative protein immobilized on a comparative support via reactions between carboxy functional groups on the comparative protein and functional groups on the comparative support, such that the covalently immobilized protein molecules are thus better able to carry out their function as compared to the comparative protein immobilized on the comparative support,
wherein the function comprises:
exposing the composition to a sample comprising a plurality of a first type of metal ion and a plurality of a second type of metal ion,
wherein following the exposing step, greater than about 90% of the first type of metal ion in the sample are sequestered by the plurality of protein molecules immobilized on the support, and
less than about 5% of the second type of metal ion in the sample are sequestered by the plurality of protein molecules immobilized on the support.

* * * * *

SEQUENCE LISTING

```
<160> NUMBER OF SEQ ID NOS: 3

<210> SEQ ID NO 1
<211> LENGTH: 92
<212> TYPE: PRT
<213> ORGANISM: Homo sapiens

<400> SEQUENCE: 1

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
            85                  90

<210> SEQ ID NO 2
<211> LENGTH: 466
<212> TYPE: DNA
<213> ORGANISM: Homo sapiens

<400> SEQUENCE: 2
accactgctg gcttttttgct gtagctccac attcctgtgc attgaggggt taacattagg      60
ctgggaagat gacaaaactt gaagagcatc tggagggaat tgtcaatatc ttccaccaat     120
actcagttcg aagggggcat tttgacaccc tctctaaggg tgagctgaag cagctgctta     180
caaaggagct tgcaaacacc atcaagaata tcaaagataa agctgtcatt gatgaaatat     240
tccaaggcct ggatgctaat caagatgaac aggtcgactt tcaagaattc atatccctgg     300
tagccattgc gctgaaggct gcccattacc acacccacaa agagtaggta gctctctgaa     360 ggcttttttac ccagcaatgt cctcaatgag ggtctttttct ttccctcacc aaaacccagc     420
cttgcccgtg gggagtaaga gttaataaac acactcacga aaagtt                    466

<210> SEQ ID NO 3
<211> LENGTH: 279
<212> TYPE: DNA
<213> ORGANISM: Homo sapiens

<400> SEQUENCE: 3
atgacgaaac tggaagaaca cttggaaggc attgttaaca tttttcatca atacagcgtg      60
cgtaagggcc acttcgacac cctgagcaaa ggtgagttga aacagctgct gaccaaagag     120
```

```
ctggcaaata cgatcaagaa tatcaaggat aaggctgtca ttgacgagat tttccagggt    180
ctggatgcca accaagacga gcaagttgat ttccaggagt ttatctccct ggtggcgatc    240
gcgctgaagg cagcgcacta tcatacccac aaagaataa                          279
```